US00PP28647P3

(12) United States Plant Patent
Pavlich

(10) Patent No.: US PP28,647 P3
(45) Date of Patent: Nov. 14, 2017

(54) ***BEGONIA* PLANT NAMED 'TNBEGTRS'**

(50) Latin Name: *Begonia rex-cultorum*
Varietal Denomination: TNBEGTRS

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/998,977

(22) Filed: Mar. 11, 2016

(65) Prior Publication Data

US 2017/0265365 P1 Sep. 14, 2017

(51) Int. Cl.
*A01H 5/02* (2006.01)

(52) U.S. Cl.
USPC ..... Plt./343

(58) Field of Classification Search
USPC ..... Plt./343
See application file for complete search history.

(56) References Cited

PUBLICATIONS

UPOV Record Detail, Stardust 1994.*
UPOV Record Detail, Stardust 1997.*

* cited by examiner

*Primary Examiner* — Keith O. Robinson
(74) *Attorney, Agent, or Firm* — Klarquist Sparkman, LLP

(57) ABSTRACT

A new and distinct form of *Begonia* plant characterized by rex type leaves with swirling leaf bases, leaves that show a subtle splatter pattern overall, leaves colored celadon green on outer half of leaf and purple red in center half, and edged in purple red in the warm temperatures, leaves colored rose red in center ⅔ and edges with a band of silver between in the colder temperatures, a dense, bushy habit, medium pink flowers in winter, and excellent vigor.

1 Drawing Sheet

Botanical denomination: *Begonia rex-cultorum.*
Variety designation: 'TNBEGTRS'.
Cross reference to: *Begonia* 'St. Nick', U.S. Plant Pat. No. 26,811.

BACKGROUND

The present invention relates to a new and distinct cultivar of *Begonia*, of the family Begoniaceae, and given the cultivar name, 'TNBEGTRS'. The new cultivar originated from a cross between a proprietary, unreleased unnamed, unpatented, rhizomatous *Begonia* seedling, as the seed parent, and an unnamed *Begonia rex-cultorum* seedling, as the pollen parent. This selection is uniquely characterized by:

1. rex type leaves with swirling leaf bases,
2. leaves show a subtle splatter pattern overall,
3. leaves colored celadon green on outer half of leaf and purple red in center half, and edged in purple red in the warm temperatures,
4. leaves colored rose red in center ⅔ and edges with a band of silver between in the colder temperatures,
5. a dense, bushy habit,
6. medium pink flowers in winter, and
7. excellent vigor.

Compared to the seed parent, a proprietary, unreleased rhizomatous *Begonia* seedling, the new cultivar has a different leaf shape and has a strongly spiral sinus and displays a subtle spatter pattern rather than defined color zones.

Compared to the pollen parent, an unnamed *Begonia rex-cultorum* seedling, the new cultivar has a different leaf shape and displays a spattered color pattern rather than a solid red color.

Compared to sibling *Begonia* 'St. Nick', U.S. Plant Pat. No. 26,811, the new cultivar has a higher crown count, less leaf lobing, and leaf colored leaves colored celadon green on outer half of leaf and purple red in center half, and edged in purple red in the warm temperatures, leaves colored rose red in center ⅔ and edges with a band of silver between in the colder temperatures, rather than with a starry red center surrounded by emerald green with white polka dots.

The new variety has been reproduced only by asexual propagation (leaf cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 10-month-old plant of *Begonia* 'TNBEGTRS' growing in a one gallon container in summer in Canby, Oreg.

FIG. 2 shows a 10-month-old plant of *Begonia* 'TNBEGTRS' growing in a one gallon container in late fall in Canby, Oreg.

DETAILED PLANT DESCRIPTION

The following is a detailed description of the new *Begonia* cultivar based on observations of two-year-old specimens grown in two gallon containers in a cool greenhouse in February in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The *Royal Horticultural Society Colour Chart,* 5$^{th}$ edition, 2007.

Plant:

*Type*.—Herbaceous rhizomatous perennial.

*Form*.—Clumping, caulescent.

*Cold hardiness*.—USDA Zone 10a.

*Size*.—Grows to 32 cm tall and 65 cm wide.

*Vigor*.—Excellent.

*Roots and rooting*.—Roots appear on leaf cuttings in 2 weeks; fine, fibrous, and white in color, White NN155A.

Stem:

*Type*.—Upright to semi-upright, congested, branching.

*Size*.—Grows to 18 cm long and 20 mm to 25 mm wide.

*# stems from base*.—18.

*Lateral branches*.—About 3 per stem.

*Internodes*.—About 0.4 mm to 10 mm long.

*Surface*.—Glabrous.

*Color*.—Brown 200B with spots of Greyed Orange 177B.

Leaf:

*Type*.—Simple.

*Arrangement*.—Alternate, congested.

*Number*.—About 90.

*Shape*.—Obliquely broadly ovate.

*Margins*.—Serrate and slightly ruffled.

*Apex*.—Acute to acuminate.

*Base*.—Oblique and spiral.

*Venation*.—Palmate, Greyed Purple N186A on topside, bottom side Greyed Purple 187B.

*Blade size*.—Grows to 17 cm wide and 22 cm long.

*Surface texture*.—Sparsely pubescent on top and pubescent on bottom side.

*Leaf strength*.—Excellent, leathery.

*Stipules*.—Deciduous, triangular, grow to 30 cm long and 8 mm wide, apex caudate, base clasping, margin entire, topside glabrous, bottom side pubescent, both sides Greyed Purple 187C.

*Petiole description*.—Grows to 25.5 cm long and 8 mm wide, succulent, pubescent, Greyed Orange 166A.

*Leaf color*.—Variable, depending on temperature, top side from petiole out — in cooler temperatures: Greyed Purple N186A along veins to Red Purple 59A to Green 136A to Red Purple 59A on the edge; the small and large (0.2 mm to 5 mm wide), red purple (Red Purple 59A) to white spots (White NN155C), with the white spots in the green area and the red purple spots in between the veins; bottom side Greyed Purple 187A; in warmer temperatures: the green area is larger and closest to Greyed Green 189B.

Inflorescence:

*Type*.—Axillary, bisexual, cyme.

*Number of flowers per cyme*.—1 to 3.

*Peduncle description*.—Grows 17 cm long and 6 mm wide, sparsely pubescent, fleshy, Greyed Brown 199B; with 2 opposite, dehiscent petiolate leaf-bracts below each cyme, cupped, oblong, 10 mm wide and 16 mm long, margins entire, tip apiculate, both sides glabrous, both sides Greyed Orange 175A.

*Pedicel description*.—Grow to 2.5 cm long, 2 mm wide, fleshy, glabrous, Red Purple 62B.

*Bloom period*.—Winter in Canby, Oreg.

Flower bud:

*Size*.—Staminate flowers 15 mm long and 14 mm wide prior to opening; pistillate flowers are 10 mm deep and 7 mm wide prior to opening.

*Shape*.—Teardrop.

*Surface texture*.—Glabrous.

*Color*.—Red Purple 63A.

Flower:

*Type*.—Monoecious, bilaterally symmetrical, single.

*Pistillate flower*.—Cupped, grows to 25 mm deep and 35 mm wide overall; 4 fleshy tepals, grow to 12 mm long and 15 mm wide, oblong, tip and base obtuse, margins entire, glabrous inside and out, Red Purple N57D inside and outside; pistil 1, 20 mm long, ovary to 25 mm wide and 11 mm deep, three winged, two equal and one longer, ovary Red Purple 62D, wings Yellow Green 145C tinted Red Purple 62D, style 3 mm long at base and Yellow Orange 22A spreading like an Elizabethan color 5 mm deep and 11 mm wide, Yellow Orange 22A, stigma convolute, Yellow Orange 18A.

*Staminate flower*.—8 mm deep and 35 mm wide, 4 tepals, Red Purple 62D inside and outside, cupped, margin entire, glabrous inside and outside, tip and base obtuse, oblong; 2 larger outer tepals 19 mm long and 18 mm wide, broadly ovate, inner tepals grow to 16 mm long and 11 mm wide, elliptic.

*Fragrance*.—None.

*Lastingness*.—A cyme blooms for about 4 weeks on the plant, flowers are self-cleaning.

Fruit and seed: None, sterile.

Diseases and pests: No known resistances to pests or diseases. No problems have been found in Canby, Oreg.

I claim:

1. A new and distinct form of *Begonia* plant as hereby illustrated and described.

* * * * *

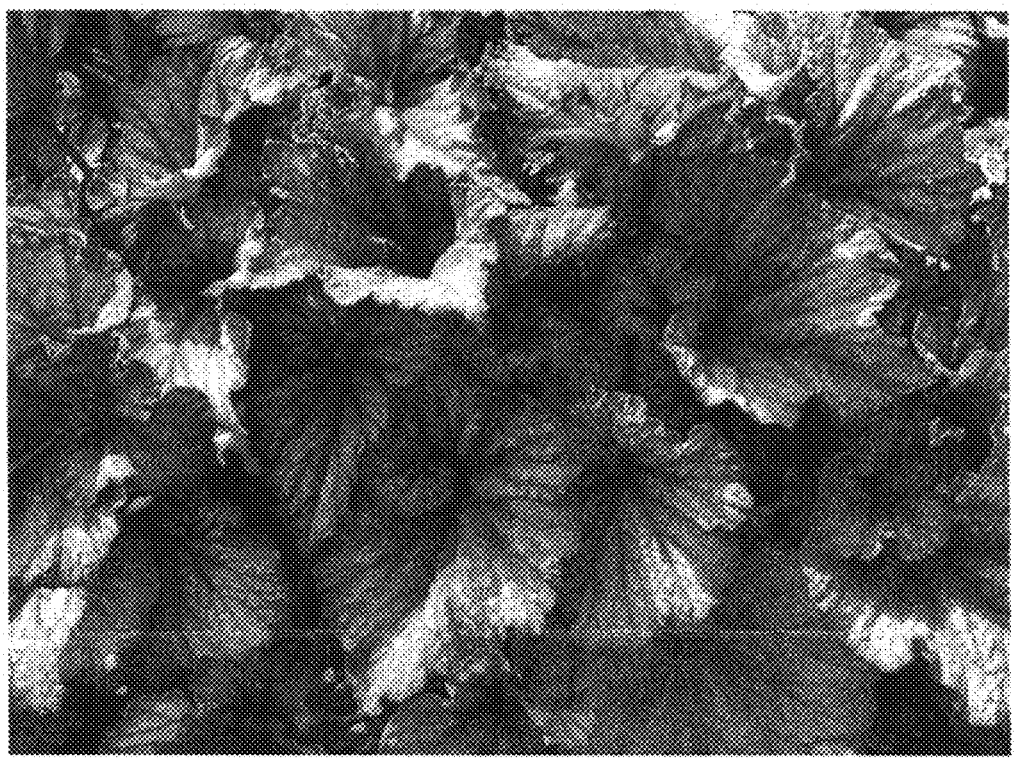

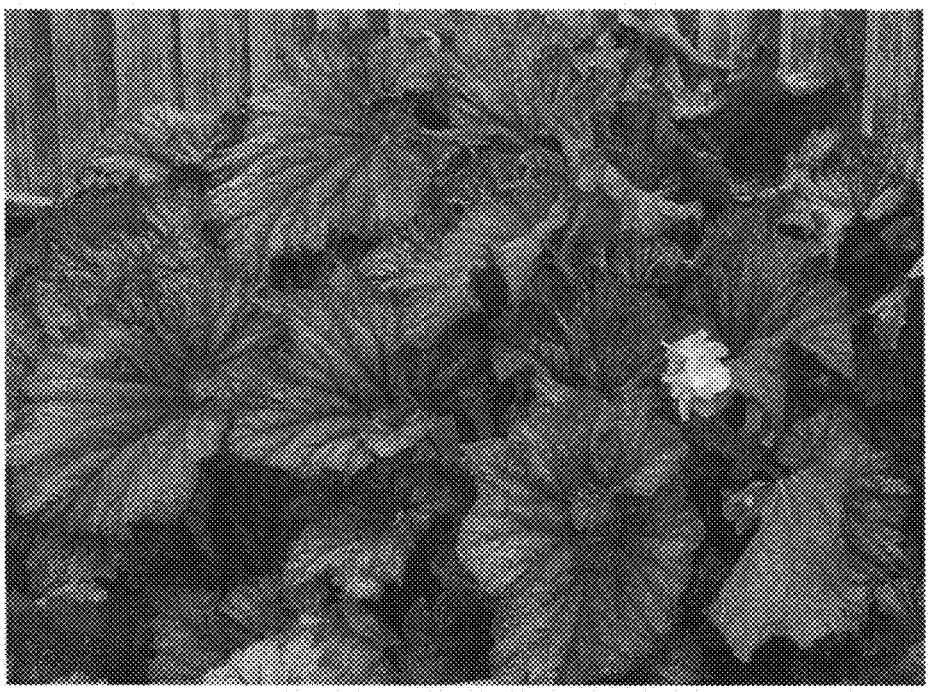
FIG. 1 above, FIG. 2 below